United States Patent
Miyake et al.

(10) Patent No.: US 10,662,166 B2
(45) Date of Patent: May 26, 2020

(54) PROCESS FOR PREPARING (2E,6Z)-2,6-NONADIENAL AND A PROCESS FOR PREPARING (2E)-CIS 6,7-EPOXY-2-NONENAL

(71) Applicant: SHIN-ETSU CHEMICAL CO., LTD., Tokyo (JP)

(72) Inventors: Yuki Miyake, Joetsu (JP); Takeshi Kinsho, Joetsu (JP); Tomohiro Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/426,738

(22) Filed: May 30, 2019

(65) Prior Publication Data

US 2019/0367468 A1    Dec. 5, 2019

(30) Foreign Application Priority Data

May 31, 2018   (JP) ................................ 2018-104778

(51) Int. Cl.
| | |
|---|---|
| *C07C 45/69* | (2006.01) |
| *C07D 301/14* | (2006.01) |
| *C07C 45/51* | (2006.01) |
| *C07C 47/277* | (2006.01) |
| *C07D 303/32* | (2006.01) |

(52) U.S. Cl.
CPC .......... *C07D 301/14* (2013.01); *C07C 45/515* (2013.01); *C07C 45/69* (2013.01); *C07C 47/277* (2013.01); *C07D 303/32* (2013.01)

(58) Field of Classification Search
CPC ...... C07C 45/515; C07C 45/69; C07D 301/14
See application file for complete search history.

(56) References Cited

PUBLICATIONS

European Search Report for Application No. 19176820.9, Patent No. 1109, dated Oct. 31, 2019.

Mark Reid et al: Two carbon homologated a,-unsaturated aldehydes from alcohols using the in situ oxidation—Wittig reaction, No. 18. dated Jan. 1, 2003. pp. 2284-2285.

Tian Xu et al: 11 Identification of a 1-6 male-produced sex-aggregation pheromone for a highly invasive cerambycid beetle. *Aromia bungii*. vol. 7. No. 1. dated Dec. 1, 2017.

Mori, K., *Pheromone Synthesis, Part 263: Synthesis of the Racemate and the Enantiomers of (3)-cis-6,7-epoxy-2-nonenal, the Male-Produced Pheromone of the Red-Necked Longhorn Beetle, Aromia bungii*, Tetrahedron 74 (2018) 1444-1448.

Xu, T. et al., *Identification of a Male-Produced Sex-Aggregation Pheromone for a Highly Invasive Cerambycid Beetle, Aromia bungii*, Scientific Reports, 7:7330 (Aug. 4, 2017) 7 pages.

*Primary Examiner* — Sikarl A Witherspoon
(74) *Attorney, Agent, or Firm* — Rimon, P.C.

(57) ABSTRACT

Provided herein are convenient and efficient processes for preparing (2E,6Z)-2,6-nonadienal and (2E)-6,7-epoxy-2-nonenal with a reduced number of steps.

For instance, provided herein is a process for preparing (2E,6Z)-2,6-nonadienal, including at least steps of subjecting a (6,6-dialkoxy-4-hexenylidene)triarylphosphorane compound of the general formula:

$Ar_3P\!=\!CH(CH_2)_2CH\!=\!CHCH(OR^1)(OR^2)$ to a Witting reaction with propanal to form a 1,1-dialkoxy-(6Z)-2,6-nonadiene compound of the general formula (6); and subjecting the 1,1-dialkoxy-(6Z)-2,6-nonadiene compound to hydrolysis to form (2E,6Z)-2,6-nonadienal. Also provided is a process for preparing (2E)-cis-6,7-epoxy-2-nonenal of the formula (8), comprising a step of subjecting (2E,6Z)-2,6-nonadienal thus obtained to epoxidation to form (2E)-cis-6, 7-epoxy-2-nonenal.

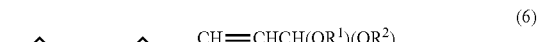

(6)

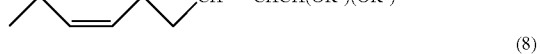

(8)

10 Claims, No Drawings

PROCESS FOR PREPARING (2E,6Z)-2,6-NONADIENAL AND A PROCESS FOR PREPARING (2E)-CIS 6,7-EPOXY-2-NONENAL

TECHNICAL FIELD

The present invention relates to a process for preparing (2E,6Z)-2,6-nonadienal which is known as a flavor or fragrance material, and a process for preparing (2E)-cis-6,7-epoxy-2-nonenal which is known as an aggregation pheromone of red-necked longhorn beetle (*Aromia bungii*) which is an insect pest to cherries.

BACKGROUND ART

The red-necked longhorn beetle (*Aromia bungii*) is a pest native in China, Taiwan, Korean peninsula and northern Vietnam, and damages trees, including cherry, persimmon, olive, peach, Japanese apricot, pomegranate and willow. It has recently invaded areas of Japan, and has damaged a number of cherry trees. A total damage is estimated to be 22 billion yen if the red-necked longhorn beetle spreads throughout Japan. Currently, the Japanese Ministry of Agriculture, Forestry and Fisheries and the Ministry of Land, Infrastructure, Transport and Tourism are trying to eliminate the red-necked longhorn beetle, but any effective control method has not been established yet. Meanwhile, control of the pest and surveillance on emergence of the pest with an aggregation pheromone are attracting attention, and a large hope is placed on its use.

Xu et al identify the aggregation pheromone of the red-necked longhorn beetle (*Aromia bungii*) as (2E)-cis-6,7-epoxy-2-nonenal (Non-Patent Literature 1). Mori reports that (2E)-cis-6,7-epoxy-2-nonenal can be synthesized by a process comprising epoxidation of 2-penten-1-ol to form 2,3-epoxy-1-pentanol, conversion of the latter into a triflate form, a coupling with an allyl Grignard reagent, and an olefin cross metathesis with 2-butenal (Non-Patent Literature 2).

LIST OF THE PRIOR ART

Non-Patent Literatures

[Non-Patent Literature 1] T. Xu et al., Scientific Reports, 2017, 7(1), 7330.
[Non-Patent Literature 2] K. Mori, Tetrahedron, 2018, 74, 1444.

SUMMARY OF THE INVENTION

However, the process described in Non-Patent Literature 2 uses an expensive Grubbs catalyst, and also requires the use of large amounts of a solvent and 2-butenal to prevent homometathesis during the olefin cross metathesis, resulting in a poor productivity which makes the process unsuitable for industrial-scale mass production. Furthermore, the overall yield in this four-step process starting from 2-penten-1-ol is as very low as 6.6%.

The present invention has been made in these circumstances, and aims to provide convenient and efficient processes with a reduced number of steps for preparing (2E,6Z)-2,6-nonadienal and (2E)-6,7-epoxy-2-nonenal.

As a result of intensive researches, the present inventors have found that (2E,6Z)-2,6-nonadienal can be conveniently prepared with a high yield and a reduced number of steps by subjecting a (6,6-dialkoxy-4-hexenylidene)triarylphosphorane compound to a Wittig reaction with propanal to form a 1,1-dialkoxy-(6Z)-2,6-nonadiene compound, followed by hydrolysis thereof, and that this process for preparing (2E, 6Z)-2,6-nonadienal can be utilized for efficient production of (2E)-cis-6,7-epoxy-2-nonenal, and thus have completed the present invention.

According to one aspect of the invention, there is provided a process for preparing (2E,6Z)-2,6-nonadienal of the following formula (7):

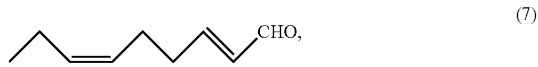

the process comprising at least steps of:
subjecting a (6,6-dialkoxy-4-hexenylidene)triarylphosphorane compound of the following general formula (4):

$$Ar_3P=CH(CH_2)_2CH=CHCH(OR^1)(OR^2) \quad (4)$$

wherein Ar may be the same or different at each occurrence and is an aryl group, and $R^1$ and $R^2$ are each independently a monovalent hydrocarbon group having 1 to 18 carbon atoms or together form a divalent hydrocarbon group, $R^1$-$R^2$, having 1 to 18 carbon atoms, to a Wittig reaction with propanal of the following formula (5):

$$CH_3CH_2CHO \quad (5)$$

to form a 1,1-dialkoxy-(6Z)-2,6-nonadiene compound of the following general formula (6):

wherein $R^1$ and $R^2$ are each independently a monovalent hydrocarbon group having 1 to 18 carbon atoms or together form a divalent hydrocarbon group, $R^1$-$R^2$, having 1 to 18 carbon atoms; and
subjecting the 1,1-dialkoxy-(6Z)-2,6-nonadiene compound to hydrolysis to form (2E,6Z)-2,6-nonadienal.

According to another aspect of the invention, there is provided a process for preparing (2E)-cis-6,7-epoxy-2-nonenal of the following formula (8):

the process comprising at least
the process for preparing (2E,6Z)-2,6-nonadienal described above; and
a step of subjecting (2E,6Z)-2,6-nonadienal to epoxidation to form (2E)-cis-6,7-epoxy-2-nonenal.

According to another aspect of the invention, there is provided a (6,6-dialkoxy-4-hexenylidene)triarylphosphorane compound of the following general formula (4):

$$Ar_3P=CH(CH_2)_2CH=CHCH(OR^1)(OR^2) \quad (4)$$

wherein Ar may be the same or different at each occurrence and is an aryl group, and $R^1$ and $R^2$ are each independently a monovalent hydrocarbon group having 1 to 18 carbon atoms or together form a divalent hydrocarbon group, $R^1$-$R^2$, having 1 to 18 carbon atoms.

According to a further aspect of the invention, there is provided a 1,1-dialkoxy-2-hexenyltriarylphosphonium halide compound of the following general formula (3):

$$X^-Ar_3P^+CH_2(CH_2)_2CH\!=\!CHCH(OR^1)(OR^2) \quad (3)$$

wherein Ar may be the same or different at each occurrence and is an aryl group, $R^1$ and $R^2$ are each independently a monovalent hydrocarbon group having 1 to 18 carbon atoms or together form a divalent hydrocarbon group, $R^1$-$R^2$, having 1 to 18 carbon atoms, and X is a halogen atom.

According to the invention, (2E,6Z)-2,6-nonadienal (2E)-6,7-epoxy-2-nonenal can be conveniently prepared with a high yield and a reduced number of process steps.

DETAILED DESCRIPTION OF THE PREFERRED EMBODIMENTS

First, there will be described the step of subjecting a (6,6-dialkoxy-4-hexenylidene)triarylphosphorane compound of the general formula (4) to a Witting reaction with propanal of formula (5) to form a 1,1-dialkoxy-(6Z)-2,6-nonadiene compound of the general formula (6) as shown below.

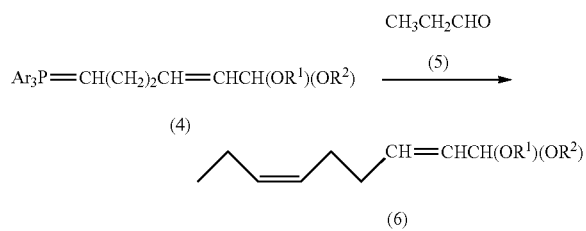

In the general formula (4) for the (6,6-dialkoxy-4-hexenylidene)triarylphosphorane compound, Ar may be same or different at each occurrence and is an aryl group. The aryl group preferably has six or seven carbon atoms. Examples of the aryl group include phenyl and tolyl groups. In view of the ease of synthesis, a phenyl group is preferred.

In the general formula (4) for the (6,6-dialkoxy-4-hexenylidene)triarylphosphorane compound, $R^1$ and $R^2$ are each independently a monovalent hydrocarbon group having 1 to 18 carbon atoms, preferably 1 to 6 carbon atoms, or together form a divalent hydrocarbon group, $R^1$-$R^2$, having 1 to 18 carbon atoms, preferably 2 to 6 carbon atoms.

Examples of the monovalent hydrocarbon groups $R^1$ and $R^2$ include linear saturated hydrocarbon groups, such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl groups; branched saturated hydrocarbon groups, such as isopropyl, 2-methylpropyl and 2-methylbutyl groups; linear unsaturated hydrocarbon groups, such as a 2-propenyl group; branched unsaturated hydrocarbon groups, such as a 2-methyl-2-propenyl group; cyclic saturated hydrocarbon groups, such as a cyclopropyl group; and isomers thereof. Apart of the hydrogen atoms in these hydrocarbon groups may be substituted with, e.g., a methyl or ethyl group.

As the monovalent hydrocarbon groups, $R^1$ and $R^2$, methyl, ethyl, n-propyl and n-butyl groups are preferred in view of the handling.

Examples of the divalent hydrocarbon group, $R^1$-$R^2$, include linear saturated hydrocarbon groups, such as ethylene, 1,3-propylene and 1,4-butylene groups; branched saturated hydrocarbon groups, such as 1,2-propylene, 2,2-dimethyl-1,3-propylene, 1,2-butylene, 1,3-butylene, 2,3-butylene and 2,3-dimethyl-2,3-butylene groups; linear unsaturated hydrocarbon groups, such as a 1-vinylethylene group; branched unsaturated hydrocarbon groups, such as a 2-methylene-1,3-propylene group; cyclic hydrocarbon groups, such as 1,2-cyclopropylene and 1,2-cyclobutylene groups; and isomers thereof. A part of the hydrogen atoms in these hydrocarbon groups may be substituted with, e.g., a methyl or ethyl group.

In view of the reactivity in the deprotection, the ease of purification, and the availability, the divalent hydrocarbon group, $R^1$-$R^2$, is preferably a lower (preferably C2-C4) hydrocarbon group. This is highly reactive, and byproducts formed in the deprotection can be easily removed by evaporation or washing with water. In view of the above, especially preferable examples of the divalent hydrocarbon group, $R^1$-$R^2$, include ethylene, 1,2-propylene, 1,3-propylene, 1,2-butylene, 1,3-butylene and 2,3-dimethyl-2,3-butylene groups.

Examples of geometric isomers of the (6,6-dialkoxy-4-hexenylidene)triarylphosphorane compound (4) include ((4Z)-6,6-dialkoxy-4-hexenylidene)triarylphosphorane and ((4E)-6,6-dialkoxy-4-hexenylidene)triarylphosphorane compounds.

Specific examples of the ((4Z)-6,6-dialkoxy-4-hexenylidene)triarylphosphorane compound include ((4Z)-6,6-diethoxy-4-hexenylidene)triphenylphosphorane, ((4Z)-6,6-dimethoxy-4-hexenylidene)triphenylphosphorane, ((4Z)-6,6-dipropoxy-4-hexenylidene)triphenylphosphorane, and ((4Z)-6,6-dibutoxy-4-hexenylidene)triphenyl phosphorane.

Specific examples of the ((4E)-6,6-dialkoxy-4-hexenylidene)triarylphosphorane compound include ((4E)-6,6-diethoxy-4-hexenylidene)triphenylphosphorane, ((4E)-6,6-dimethoxy-4-hexenylidene)triphenylphosphorane, ((4E)-6,6-dipropoxy-4-hexenylidene)triphenylphosphorane, and ((4E)-6,6-dibutoxy-4-hexenylidene)triphenyl phosphorane.

For an economical reason, preferable (6,6-dialkoxy-4-hexenylidene)triarylphosphorane compounds (4) are (6,6-dialkoxy-4-hexenylidene)triphenylphosphorane compounds, such as ((4Z)-6,6-diethoxy-4-hexenylidene)triphenylphosphorane, ((4Z)-6,6-dimethoxy-4-hexenylidene)triphenylphosphorane, ((4E)-6,6-diethoxy-4-hexenylidene)triphenylphosphorane and ((4E)-6,6-dimethoxy-4-hexenylidene)triphenylphosphorane.

The (6,6-dialkoxy-4-hexenylidene)triarylphosphorane compound (4) may be prepared by nucleophilic substitution between a 6-halo-1,1-dialkoxy-2-hexene compound of the following general formula (1) and a triarylphosphine compound of the general formula (2) to form 1,1-dialkoxy-2-hexenyltriarylphosphonium halide compound of the general formula (3), followed by deprotonation of the 1,1-dialkoxy-2-hexenyltriarylphosphonium halide compound (3) in the presence of a base to form a (6,6-dialkoxy-4-hexenylidene) triarylphosphorane compound (4), as shown below.

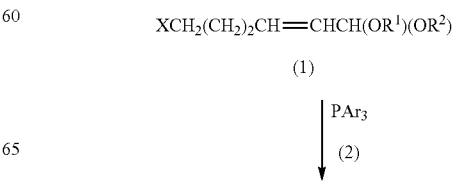

-continued

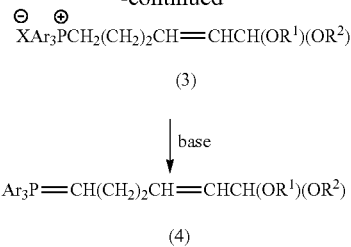

In the general formula (1) for the 6-halo-1,1-dialkoxy-2-hexene compound, X is a halogen atom. Examples of the halogen atom include fluorine, chlorine, bromine and iodine atoms. In view of the ease of handling and the ease of preparing the 1,1-dialkoxy-2-hexenyltriarylphosphonium halide compound (3), chlorine, bromine and iodine atoms are preferred.

In the general formula (1) for the 6-halo-1,1-dialkoxy-2-hexene compound, $R^1$ and $R^2$ are as defined for the (6,6-dialkoxy-4-hexenylidene)triarylphosphorane of the general formula (4).

Examples of geometric isomers of the 6-halo-1,1-dialkoxy-2-hexene compound (1) include (2E)-6-halo-1,1-dialkoxy-2-hexene compounds and (2Z)-6-halo-1,1-dialkoxy-2-hexene compounds.

Specific examples of the (2E)-6-halo-1,1-dialkoxy-2-hexene compound include (2E)-6-chloro-1,1-dialkoxy-2-hexene compounds, such as (2E)-6-chloro-1,1-diethoxy-2-hexene, (2E)-6-chloro-1,1-dimethoxy-2-hexene, (2E)-6-chloro-1,1-dipropoxy-2-hexene, and (2E)-6-chloro-1,1-dibutoxy-2-hexene; (2E)-6-bromo-1,1-dialkoxy-2-hexene compounds, such as (2E)-6-bromo-1,1-diethoxy-2-hexene, (2E)-6-bromo-1,1-dimethoxy-2-hexene, (2E)-6-bromo-1,1-dipropoxy-2-hexene, and (2E)-6-bromo-1,1-dibutoxy-2-hexene; and (2E)-6-iodo-1,1-dialkoxy-2-hexene compounds, such as (2E)-6-iodo-1,1-diethoxy-2-hexene, (2E)-6-iodo-1,1-dimethoxy-2-hexene, (2E)-6-iodo-1,1-dipropoxy-2-hexene, and (2E)-6-iodo-1,1-dibutoxy-2-hexene.

Specific examples of the (2Z)-6-halo-1,1-dialkoxy-2-hexene compound include (2Z)-6-chloro-1,1-dialkoxy-2-hexene compounds, such as (2Z)-6-chloro-1,1-diethoxy-2-hexene, (2Z)-6-chloro-1,1-dimethoxy-2-hexene, (2Z)-6-chloro-1,1-dipropoxy-2-hexene, and (2Z)-6-chloro-1,1-dibutoxy-2-hexene; (2Z)-6-bromo-1,1-dialkoxy-2-hexene compounds, such as (2Z)-6-bromo-1,1-diethoxy-2-hexene, (2Z)-6-bromo-1,1-dimethoxy-2-hexene, (2Z)-6-bromo-1,1-dipropoxy-2-hexene, and (2Z)-6-bromo-1,1-dibutoxy-2-hexene; and (2Z)-6-iodo-1,1-dialkoxy-2-hexene compounds such as (2Z)-6-iodo-1,1-diethoxy-2-hexene, (2Z)-6-iodo-1,1-dimethoxy-2-hexene, (2Z)-6-iodo-1,1-dipropoxy-2-hexene, and (2Z)-6-iodo-1,1-dibutoxy-2-hexene.

For an economical reason, preferable 6-halo-1,1-dialkoxy-2-hexene compounds (1) are 6-chloro-1,1-dialkoxy-2-hexene compound, such as (2Z)-6-chloro-1,1-diethoxy-2-hexene, (2Z)-6-chloro-1,1-dimethoxy-2-hexene, (2E)-6-chloro-1,1-diethoxy-2-hexene, and (2E)-6-chloro-1,1-dimethoxy-2-hexene. As the 6-halo-1,1-dialkoxy-2-hexene compound (1), a commercially available one may be used, or it may be synthesized.

Because (2E,6Z)-2,6-nonadienal (7) can be prepared in a convergent manner by hydrolysis as described later, use may be made either of E- and Z-isomers of the 6-halo-1,1-dialkoxy-2-hexene compound (1), or both of them, i.e., a mixture of geometric isomers.

In the general formula (2) for the triarylphosphine compound, Ar is as defined for the (6,6-dialkoxy-4-hexenylidene)triarylphosphorane of the general formula (4). Specific examples of the triarylphosphine compound (2) include triphenylphosphine and tritolylphosphine. In view of the reactivity, triphenylphosphine is preferred.

The amount of the triarylphosphine compound (2) to be used may range preferably from 0.8 to 2.0 mol per mol of the 6-halo-1,1-dialkoxy-2-hexene compound (1), in view of the reactivity. If necessary, two or more triarylphosphine compounds (2) may be used in combination. A commercially available triarylphosphine compound may be used.

A halide compound may be added, if necessary, in the preparation of the 1,1-dialkoxy-2-hexenyltriarylphosphonium halide compound (3). Although the reaction proceeds even without the addition of the halide compound, the duration required for the reaction can be shortened by the addition of a halide compound.

Examples of the halide compound include alkali metal halides, such as sodium iodide, potassium iodide, sodium bromide and potassium bromide. In view of the reactivity, alkali metal iodides, such as sodium iodide and potassium iodide, are preferred. The halide compound may be used alone.

The amount of the halide compound to be used may range preferably from 1.0 to 2.0 mol per mol of the 6-halo-1,1-dialkoxy-2-hexene compound (1), in view of the reactivity. If necessary, two or more halides may be used in combination. A commercially available halide may be used.

To prevent hydrolysis of the acetal due to the reaction system becoming acid, a base may be added to the reaction system, provided that the base should be such that does not participate in the deprotonation. Examples of such a base include alkali metal carbonates, such as potassium carbonate, sodium carbonate; and alkaline earth metal carbonates, such as calcium carbonate.

A solvent may be used in the preparation of the 1,1-dialkoxy-2-hexenyltriarylphosphonium halide compound (3). Examples of the solvent to be used include hydrocarbon solvents, such as toluene, xylene and hexane; ether solvents, such as tetrahydrofuran, 4-methyltetrahydropyran and diethyl ether; and polar solvents, such as N,N-dimethylformamide, N,N-dimethylacetamide and acetonitrile. Ether solvents, such as tetrahydrofuran, and polar solvents, such as acetonitrile, N,N-dimethylformamide, and N,N-dimethylacetamide, are preferred in view of the reactivity. The solvent may be used alone or in combination. A commercially available solvent may be used.

The amount of the solvent to be used may range preferably from 300 to 4,000 g per mol of the 6-halo-1,1-dialkoxy-2-hexene compound (1), in view of the reactivity.

An optimal reaction temperature during the preparation of the 1,1-dialkoxy-2-hexenyltriarylphosphonium halide compound (3) may vary, depending on the type of the solvent to be used. It ranges preferably from 60 to 180° C. in view of the reaction rate.

A duration of the reaction for the preparation of the 1,1-dialkoxy-2-hexenyl triarylphosphonium halide compound (3) may vary, depending on the type of the solvent and a scale of the reaction system. It ranges preferably from 5 to 35 hours in view of the reactivity.

Examples of geometric isomers of the 1,1-dialkoxy-2-hexenyltriarylphosphonium halide compound (3) include (2Z)-1,1-dialkoxy-2-hexenyltriarylphosphonium halide compounds and (2E)-1,1-dialkoxy-2-hexenyl triarylphosphonium halide compounds.

Examples of the (2Z)-1,1-dialkoxy-2-hexenyltriarylphosphonium halide compound include (2Z)-1,1-dialkoxy-2-hexenyltriarylphosphonium bromide compounds, such as (2Z)-1,1-diethoxy-2-hexenyltriarylphosphonium bromide, (2Z)-1,1-dimethoxy-2-hexenyltriarylphosphonium bromide, (2Z)-1,1-dipropoxy-2-hexenyltriarylphosphonium bromide, and (2Z)-1,1-dibutoxy-2-hexenyltriarylphosphonium bromide; and (2Z)-1,1-dialkoxy-2-hexenyltriarylphosphonium iodide compounds, such as (2Z)-1,1-diethoxy-2-hexenyltriarylphosphonium iodide, (2Z)-1,1-dimethoxy-2-hexenyltriarylphosphonium iodide, (2Z)-1,1-dipropoxy-2-hexenyltriarylphosphonium iodide, and (2Z)-1,1-dibutoxy-2-hexenyltriarylphosphonium iodide.

Examples of the (2E)-1,1-dialkoxy-2-hexenyltriarylphosphonium halide compound include (2E)-1,1-dialkoxy-2-hexenyltriarylphosphonium bromide compounds, such as (2E)-1,1-diethoxy-2-hexenyltriarylphosphonium bromide, (2E)-1,1-dimethoxy-2-hexenyltriarylphosphonium bromide, (2E)-1,1-dipropoxy-2-hexenyltriarylphosphonium bromide, and (2E)-1,1-dibutoxy-2-hexenyltriarylphosphonium bromide; and (2E)-1,1-dialkoxy-2-hexenyltriarylphosphonium iodide compounds, such as (2E)-1,1-diethoxy-2-hexenyltriarylphosphonium iodide, (2E)-1,1-dimethoxy-2-hexenyltriarylphosphonium iodide, (2E)-1,1-dipropoxy-2-hexenyltriarylphosphonium iodide, and (2E)-1,1-dibutoxy-2-hexenyltriarylphosphonium iodide.

Examples of the base to be used in the preparation of the (6,6-dialkoxy-4-hexenylidene)triarylphosphorane compound (4) include alkyllithium compounds, such as n-butyllithium and tert-butyllithium; metal alkoxides, such as potassium tert-butoxide, sodium tert-butoxide, potassium methoxide, sodium methoxide, potassium ethoxide and sodium ethoxide; metal amides, such as lithium diisopropylamide and sodium bis(trimethylsilyl)amide; and metal hydrides, such as sodium hydride and potassium hydride. In view of the reactivity, metal alkoxides are preferred, and potassium tert-butoxide, sodium methoxide and sodium ethoxide are more preferred.

The amount of the base to be used may range preferably from 0.8 to 2.0 mol per mol of the 6-halo-1,1-dialkoxy-2-hexene compound (1), in view of the reactivity. The base may be used alone or in combination. A commercially available base may be used.

A solvent may be used in the preparation of the (6,6-dialkoxy-4-hexenylidene)triarylphosphorane compound (4). Examples of the solvent to be used include those mentioned for the preparation of the (1,1-dialkoxy-2-hexenyltriarylphosphonium halide compound (3). The type and amount of the solvent to be used may be same as or different from those used in the preparation of the 1,1-dialkoxy-2-hexenyltriarylphosphonium halide compound (3).

An optimal reaction temperature during the preparation of the (6,6-dialkoxy-4-hexenylidene)triarylphosphorane compound (4) may vary, depending on the types of the solvent and the base to be used. It ranges preferably from −78 to 25° C. in view of the reactivity.

A duration of the reaction for the preparation of the (6,6-dialkoxy-4-hexenylidene)triarylphosphorane compound (4) may vary, depending on the type of the solvent and a scale of the reaction system. It ranges preferably from 0.5 to 6 hours.

The 1,1-dialkoxy-2-hexenyltriarylphosphonium halide compound (3) may be used without isolation after prepared, for the deprotonation with the base to form the (6,6-dialkoxy-4-hexenylidene)triarylphosphorane compound (4), or may be isolated prior to the deprotonation with the base to form the (6,6-dialkoxy-4-hexenylidene)triarylphosphorane compound (4).

The amount of propanal (5) to be used may range preferably from 0.9 to 2.0 mol, more preferably from 0.9 to 1.5 mol, per mol of the (6,6-dialkoxy-4-hexenylidene)triarylphosphorane compound (4), in view of the yield.

In a case where the (6,6-dialkoxy-4-hexenylidene)triarylphosphorane compound (4) is prepared from the 6-halo-1,1-dialkoxy-2-hexene compound (1) and is used without isolation in the Wittig reaction, the amount of propanal to be used per mol of the 6-halo-1,1-dialkoxy-2-hexene compound (1) is as described above. A commercially available propanal (5) may be used, or it may be synthesized.

A solvent may be used in the Wittig reaction. Examples of the solvent to be used in the Wittig reaction include those mentioned for the preparation of the 1,1-dialkoxy-2-hexenyltriarylphosphonium halide compound (3). The type and amount of the solvent to be used may be same as or different from those used for the preparation of the (6,6-dialkoxy-4-hexenylidene)triarylphosphorane compound (4).

An optimal temperature during the Wittig reaction may vary, depending on the type of the solvent to be used. It ranges preferably from −78 to 25° C., more preferably from −78 to 10° C., still more preferably from −70 to 5° C., for the stereoselective production of the 1,1-dialkoxy-(6Z)-2,6-nonadiene compound (6).

A duration of the Wittig reaction may vary, depending on a scale of the reaction system. It ranges preferably from 0.5 to 15 hours.

Examples of geometric isomers of the 1,1-dialkoxy-(6Z)-2,6-nonadiene compound (6) include 1,1-dialkoxy-(2E,6Z)-2,6-nonadiene compounds and 1,1-dialkoxy-(2Z,6Z)-2,6-nonadiene compounds.

Examples of the 1,1-dialkoxy-(2E,6Z)-2,6-nonadiene compound include 1,1-dimethoxy-(2E,6Z)-2,6-nonadiene, 1,1-diethoxy-(2E,6Z)-2,6-nonadiene, 1,1-dipropoxy-(2E,6Z)-2,6-nonadiene, and 1,1-dibutoxy-(2E,6Z)-2,6-nonadiene.

Examples of the 1,1-dialkoxy-(2Z,6Z)-2,6-nonadiene compound include 1,1-dimethoxy-(2Z,6Z)-2,6-nonadiene, 1,1-diethoxy-(2Z,6Z)-2,6-nonadiene, 1,1-dipropoxy-(2Z,6Z)-2,6-nonadiene, and 1,1-dibutoxy-(2Z,6Z)-2,6-nonadiene.

For an economical reason, preferable 1,1-dialkoxy-(6Z)-2,6-nonadiene compounds (6) are 1,1-dimethoxy-(6Z)-2,6-nonadiene compounds, such as 1,1-dimethoxy-(2Z,6Z)-2,6-nonadiene, and 1,1-dimethoxy-(2E,6Z)-2,6-nonadiene, and 1,1-diethoxy-(6Z)-2,6-nonadiene compounds, such as 1,1-diethoxy-(2Z,6Z)-2,6-nonadiene, and 1,1-diethoxy-(2E,6Z)-2,6-nonadiene.

Next, there will be described the step of subjecting the 1,1-dialkoxy-(6Z)-2,6-nonadiene compound of the general formula (6) to hydrolysis to form (2E,6Z)-2,6-nonadienal of the formula (7) as shown below.

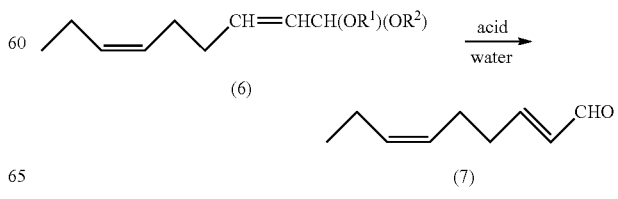

The hydrolysis may be carried out using an acid, water, and optionally a solvent.

Examples of the acid to be used in the hydrolysis include mineral acids, such as hydrochloric acid and hydrobromic acid; and p-toluenesulfonic acid, trifluoroacetic acid, acetic acid, formic acid, oxalic acid, iodo(trimethyl)silane, and titanium tetrachloride. Hydrochloric acid is preferred in view of the reactivity.

The amount of the acid to be used in the hydrolysis may range preferably from 0.01 to 15.00 mol per mol of the 1,1-dialkoxy-(6Z)-2,6-nonadiene compound (6) in view of the reactivity. The acid may be used alone or in combination. A commercially available acid may be used.

The amount of water to be used in the hydrolysis may range preferably from 18 to 3,000 g per mol of the 1,1-dialkoxy-(6Z)-2,6-nonadiene compound (6), in view of the reactivity.

Examples of the solvent to be used in the hydrolysis include hydrocarbon solvents, such as toluene, xylene and hexane; ether solvents, such as tetrahydrofuran, 4-methyltetrahydropyran and diethyl ether; polar solvents, such as N,N-dimethylformamide, N,N-dimethylacetamide, acetonitrile, dichloromethane and chloroform; and alcohol solvents, such as methanol and ethanol. The solvent may be used alone or in combination. A commercially available solvent may be used.

An optimal solvent may vary, depending on the type of the acid to be used. In view of the reactivity, tetrahydrofuran may be preferably used when oxalic acid is used as the acid. When hydrochloric acid is used as the acid, no solvent or a hydrocarbon solvent, such as hexane, may be preferably used.

The amount of the solvent to be used may range preferably from 0 to 3,000 g per mol of the 1,1-dialkoxy-(6Z)-2,6-nonadiene compound (6), in view of the reactivity.

The temperature during the hydrolysis may vary, depending on the type of the solvent to be used. It ranges preferably from −20 to 150° C. in view of the reactivity.

The duration of the hydrolysis may vary, depending on the type of the solvent and a scale of the reaction system. It ranges preferably from 0.5 to 15 hours in view of the reactivity.

The aqueous solution in the hydrolysis reaction may preferably have a pH of 1.0 or less, more preferably from −1.0 to +1.0, so as to allow isomerization to proceed sufficiently to thereby produce (2E,6Z)-2,6-nonadienal (7) of high isomeric purity in an E-stereoselective manner. The pH may be determined with a pH test paper or a pH meter while adjusting a temperature of the liquid to be measured at 25° C.

In this way, the olefin stereochemistry at the position 2 in 1,1-dialkoxy-(6Z)-2,6-nonadiene compound converges almost completely to the E-form by the isomerization of the conjugated aldehyde generated by the hydrolysis. Even if the olefin at the position 2 is rearranged to the position 3 during the hydrolysis due to effect of the acetal structure, it converges to a more stable conjugated aldehyde of the E-form, so that a high-purity (2E,6Z)-2,6-nonadienal product (7) can be obtained with less impurities.

The process described above is very useful for industrial production, because (2E,6Z)-2,6-nonadienal (7) can be produced in a highly Z-selective manner at the position 6 in the Wittig reaction and in a highly E-selective manner at the position 2 in the isomerization of conjugated aldehyde, as described above.

The Wittig reaction step and the hydrolysis step may be carried out separately, or the hydrolysis step may be carried out in situ subsequent to the Wittig reaction step in a consecutive manner (one-pot synthesis). By conducting the reactions in a consecutive manner, time for work-up, concentration and recharging can be saved. It has also been found that (2E,6Z)-2,6-nonadienal (7) can be produced at an improved yield by conducting the reactions in a consecutive manner. It is considered that this is because the loss of the 1,1-dialkoxy-(6Z)-2,6-nonadiene compound (6) into the aqueous phase in washing can be avoided and, further, because decomposition or polymerization of the 1,1-dialkoxy-(6Z)-2,6-nonadiene compound (6), which may happen when the reaction product obtained by the work-up in a crude state after the Wittig reaction is subjected to a concentration step, can be avoided.

The Wittig reaction step and the hydrolysis step can be carried out in a consecutive manner by adding the acid and water to the reaction system at the end of the Witting reaction.

In a case where the hydrolysis step is carried out in situ subsequent to the Wittig reaction step, the amount of the acid to be used may range preferably from 0.10 to 5.00 mol per mol of the 1,1-dialkoxy-(6Z)-2,6-nonadiene compound (6), in view of the yield of (2E,6Z)-2,6-nonadienal (7).

In a case where the hydrolysis step is carried out in situ subsequent to the Wittig reaction step, the amount of the solvent to be used may range preferably from 1000 to 3,000 g per mol of the 1,1-dialkoxy-(6Z)-2,6-nonadiene compound (6), in view of the yield of (2E,6Z)-2,6-nonadienal (7).

In a case where the hydrolysis step is carried out in situ subsequent to the Wittig reaction step, the amount of water to be used may range preferably from 18 to 2,000 g per mol of the 1,1-dialkoxy-(6Z)-2,6-nonadiene compound (6), in view of the yield of (2E,6Z)-2,6-nonadienal (7).

In a case where the hydrolysis step is carried out in situ subsequent to the Wittig reaction step, the reactant concentration, i.e., the moles of the 1,1-dialkoxy-(6Z)-2,6-nonadiene compound (6) relative to a total weight (g) of the solvent and water, may range preferably from $1.5 \times 10^{-4}$ to $2.5 \times 10^{-4}$ mol/g, in view of the yield of (2E,6Z)-2,6-nonadienal (7).

In a case where the hydrolysis step is carried out in situ subsequent to the Wittig reaction step, the temperature during the hydrolysis may range preferably from 0 to 30° C., in view of the yield of (2E,6Z)-2,6-nonadienal (7).

In a case where the hydrolysis step is carried out in situ subsequent to the Wittig reaction step, the duration of the hydrolysis reaction may range preferably from 0.5 to 3 hours.

Next, there will be described the step of subjecting (2E,6Z)-2,6-nonadienal of formula (7) to epoxidation to form (2E)-cis-6,7-epoxy-2-nonenal of formula (8), as shown below.

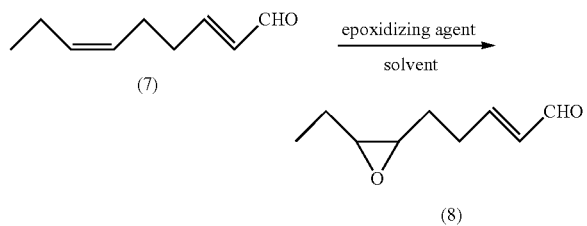

The epoxidation may be carried out by subjecting (2E, 6Z)-2,6-nonadienal (7) to a reaction with an epoxidizing agent in a solvent.

Examples of the epoxidizing agent used for the epoxidation include percarboxylic acid compounds having 1 to 7 carbon atoms, such as meta-chloroperoxybenzoic acid (MCPBA), performic acid and peracetic acid; and dioxirane compounds, such as dimethyldioxirane and methyl(trifluoromethyl)dioxirane. In view of the ease of handling, meta-chloroperoxybenzoic acid is preferred.

The amount of the epoxidizing agent to be used may range preferably from 1.0 to 2.0 mol per mol of (2E,6Z)-2,6-nonadienal (7), in view of the reactivity. The epoxidizing agent may be used alone or in combination. A commercially available epoxidizing agent may be used.

It is also possible to cause asymmetric epoxidation in the conditions of the Jacobsen-Kazuki epoxidation or the conditions of the Shi asymmetric epoxidation.

In a case where a percarboxylic acid compound is used as the epoxidizing agent, an alkali metal hydrogen carbonate, such as sodium hydrogen carbonate, may be used, if necessary, to prevent the reaction system from becoming acid due to carboxylic acid compounds derived from the percarboxylic acid compound.

Examples of the solvent to be used in the epoxidation include hydrocarbon solvents, such as toluene and hexane; ether solvents, such as tetrahydrofuran, 4-methyltetrahydropyran and diethyl ether; and polar solvents, such as dichloromethane and acetonitrile. The solvent may be used alone or in combination. A commercially available solvent may be used. An optimal solvent may vary, depending on the type of the epoxidizing agent to be used. A polar solvent, such as dichloromethane, may be preferably used in view of the reactivity, when meta-chloroperoxybenzoic acid is used as the epoxidizing agent.

The amount of the solvent to be used may range preferably from 100 to 8,000 g per mol of (2E,6Z)-2,6-nonadienal (7), in view of the reactivity.

The reaction temperature during the epoxidation may vary, depending on the type of the solvent to be used. It ranges preferably from −30 to 50° C. in view of the reactivity.

The duration of the reaction for the epoxidation may vary, depending on the type of the solvent and a scale of the reaction system. It ranges preferably from 1 to 30 hours in view of the productivity.

Examples of (2E)-cis-6,7-epoxy-2-nonenal (8) include (2E,6R,7S)-6,7-epoxy-2-nonenal of formula (8-1) below, (2E,6S,7R)-6,7-epoxy-2-nonenal of formula (8-2) below, and a racemic mixture and schalemic mixtures thereof.

(8-1)

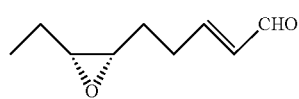

(8-2)

EXAMPLES

The invention will be further described with reference to the following Examples. It should be construed that the invention is not limited to or by Examples.

Example 1

Preparation of (2E,6Z)-2,6-nonadienal (7)(First Embodiment)

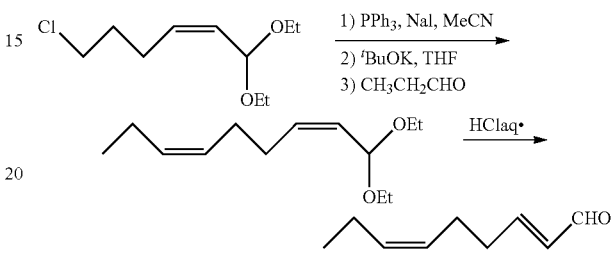

To a reactor were added (2Z)-6-chloro-1,1-diethoxy-2-hexene (1-1: X=Cl) (140.56 g, 0.68 mol), sodium iodide (104.92 g, 0.70 mol), triphenylphosphine (174.42 g, 0.67 mol), and acetonitrile (673.56 g) at room temperature. The resulting mixture was stirred under reflux at 75 to 85° C. for 13 hours to obtain (2Z)-1,1-diethoxy-2-hexenyltriphenylphosphonium iodide. After cooled to 30 to 40° C., tetrahydrofuran (1211.50 g) was added. The resulting mixture was cooled to −60° C., followed by the addition of potassium tert-butoxide (70.69 g, 0.63 mol). Then, the mixture was stirred for 1 hour to obtain ((4Z)-6,6-diethoxy-4-hexenylidene)triphenylphosphorane. Then, propanal (45.63 g, 0.77 mol) was added dropwise over 20 minutes. After completion of the dropwise addition, the mixture was stirred at −60° C. for 90 minutes to obtain 1,1-diethoxy-(2Z,6Z)-2,6-nonadiene. Then, the mixture was warmed to 20° C., and the reaction was stopped by the addition of pure water (1061 g) and sodium chloride (106.1 g). After removal of the aqueous layer by liquid-liquid separation, the organic layer was concentrated by evaporating the solvent under vacuum to obtain a concentrate (91.15 g).

The concentrate thus obtained was added together with water (48.76 g) to a reactor at room temperature. While stirring the mixture, 20 wt % hydrochloric acid (75.51 g) was added dropwise over 40 minutes. After completion of the dropwise addition, the mixture was stirred for 6 hours at room temperature. Hexane (56.71 g) was added to the reactor. After the reaction liquid was stirred for 30 minutes, the aqueous layer was removed by liquid-liquid separation. The aqueous solution in the hydrolysis reaction mixture had a pH of less than 1 as determined with a pH test paper. The organic layer thus obtained was concentrated by evaporating the solvent under vacuum, and the resulting concentrate was subjected to distillation under vacuum to obtain (2E,6Z)-2, 6-nonadienal (7) (37.32 g, 0.27 mol) with a yield of two-step process of 39.7%.

Characterization of (2E,6Z)-2,6-Nonadienal (7)

[NMR Spectra] $^1$H-NMR (500 MHz, CDCl$_3$): δ0.94 (3H, t, J=7.7 Hz), 2.02 (2H, dt, J=7.7, 7.3 Hz), 2.24 (2H, td, J=7.3, 7.3 Hz), 2.38 (2H, tdd, J=7.3, 7.3, 1.5 Hz), 5.26-5.31 (1H, m), 5.40-5.45 (1H, m), 6.11 (1H, ddt, J=15.7, 8.0, 1.5 Hz), 6.82 (1H, dt, J=15.7, 6.9 Hz), 9.48 (1H, d, J=8.0 Hz);

$^{13}$C-NMR (75.6 MHz, CDCl$_3$): 14.12, 20.50, 25.35, 32.66, 126.66, 133.14, 133.23, 158.01, 193.95

[Mass Spectrum] EI-Mass Spectrum (70 eV): m/z 138 (M+), 123, 109, 95, 81, 67, 53, 41, 27

[IR Absorption Spectrum] (NaCl): vmax 3008, 2964, 2934, 2874, 2735, 1694, 1638, 1456, 1303, 1175, 1133, 1105, 973, 719, 565

Example 2

Preparation of (2E,6Z)-2,6-nonadienal (7) (Second Embodiment)

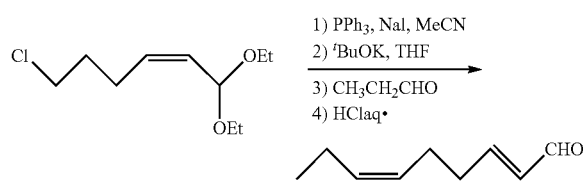

To a reactor were added (2Z)-6-chloro-1,1-diethoxy-2-hexene (1-1: X=Cl) (140.56 g, 0.68 mol), sodium iodide (104.92 g, 0.70 mol), triphenylphosphine (174.42 g, 0.67 mol), and acetonitrile (673.56 g) at room temperature. The resulting mixture was stirred under reflux at 75 to 85° C. for 14 hours to obtain (2Z)-1,1-diethoxy-2-hexenyltriphenylphosphonium iodide. After cooled to 30 to 40° C., tetrahydrofuran (1211.50 g) was added. The resulting mixture was cooled to −60° C., followed by the addition of potassium tert-butoxide (70.69 g, 0.63 mol). Then, the mixture was stirred for 1 hour to obtain ((4Z)-6,6-diethoxy-4-hexenylidene)triphenylphosphorane. Then, propanal (45.63 g, 0.77 mol) was added dropwise over 20 minutes. After completion of the dropwise addition, the mixture was stirred at −60° C. for 50 minutes to obtain 1,1-diethoxy-(2Z,6Z)-2,6-nonadiene. Then, the mixture was warmed to 20° C. To the same reactor were added pure water (1061 g), hexane (424 g), and 20 wt % hydrochloric acid (200 g). After the reaction liquid was stirred for 30 minutes, sodium chloride (106.1 g) was added. The aqueous layer was removed by liquid-liquid separation. The aqueous solution in the hydrolysis reaction mixture had a pH of less than 1 as determined with a pH test paper. The organic layer thus obtained was concentrated by evaporating the solvent under vacuum, and the resulting concentrate was subjected to distillation under vacuum to obtain (2E,6Z)-2,6-nonadienal (7) (52.56 g, 0.38 mol) with a yield of two-step process of 56.0%.

Example 3

Preparation of (2E)-cis-6,7-epoxy-2-nonenal (8)

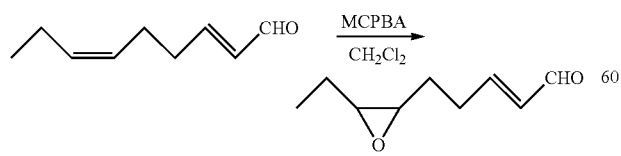

To a reactor were added (2E,6Z)-2,6-nonadienal (7) (15.88 g, 0.115 mol) and dichloromethane (571 g) at room temperature. The resulting mixture was stirred at 0 to 5° C. for 30 minutes. Then, meta-chloroperoxybenzoic acid (43.92 g, 0.165 mol) was added at 0 to 5° C., followed by stirring at 25° C. for 3 hours. After the reaction liquid was cooled to 5° C. or below, the reaction was stopped by the addition of sodium thiosulfate (12.91 g), water (119.24 g), and a 25 wt % aqueous sodium hydroxide solution (19.87 g). After removal of the aqueous layer by liquid-liquid separation, the organic layer was concentrated by evaporating the solvent under vacuum, and the resulting concentrate was purified by column chromatography (ethyl acetate/n-hexane=5/1) to obtain (2E)-cis-6,7-epoxy-2-nonenal (8) (15.07 g, 0.0978 mol) with a yield of 85.0%.

Characterization of (2E)-cis-6,7-epoxy-2-nonenal (8)

[NMR Spectra] $^1$H-NMR (500 MHz, CDCl$_3$): δ1.01 (3H, t, J=7.7 Hz), 1.43-1.59 (2H, m), 1.61-1.68 (1H, m), 1.73-1.80 (1H, m), 2.44-2.57 (2H, m), 2.88 (1H, td, J=6.5, 4.2 Hz), 2.92 (1H, td, J=7.3, 4.2 Hz), 6.13 (1H, ddt, J=15.7, 7.7, 1.5 Hz), 6.87 (1H, dt, J=15.7, 6.9 Hz), 9.49 (1H, d, J=7.7 Hz); $^{13}$C-NMR (75.6 MHz, CDCl$_3$): 10.47, 21.02, 26.15, 29.80, 56.17, 58.26, 133.27, 156.85, 193.72.

[Mass Spectrum] EI-Mass Spectrum (70 eV): m/z 154 (M+), 136, 125, 112, 97, 85, 67, 55, 41, 29.

[IR Absorption Spectrum] (NaCl): vmax 2972, 2937, 2878, 2818, 2737, 1691, 1638, 1458, 1391, 1308, 1273, 1130, 1095, 1016, 976, 905, 816.

The invention claimed is:

1. A process for preparing (2E,6Z)-2,6-nonadienal of the following formula (7):

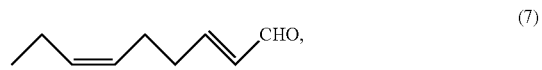

the process comprising at least steps of:
subjecting a (6,6-dialkoxy-4-hexenylidene)triarylphosphorane compound of the following general formula (4):

Ar$_3$P═CH(CH$_2$)$_2$CH═CHCH(OR$^1$)(OR$^2$)     (4)

wherein Ar may be the same or different at each occurrence and is an aryl group, and R$^1$ and R$^2$ are each independently a monovalent hydrocarbon group having 1 to 18 carbon atoms or together form a divalent hydrocarbon group, R$^1$-R$^2$, having 1 to 18 carbon atoms, to a Wittig reaction with propanal of the following formula (5):

CH$_3$CH$_2$CHO     (5)

to form a 1,1-dialkoxy-(6Z)-2,6-nonadiene compound of the following general formula (6):

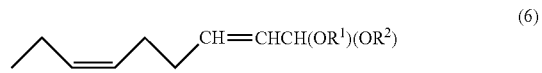

wherein R$^1$ and R$^2$ are each independently a monovalent hydrocarbon group having 1 to 18 carbon atoms or together form a divalent hydrocarbon group, R$^1$-R$^2$, having 1 to 18 carbon atoms; and
subjecting the 1,1-dialkoxy-(6Z)-2,6-nonadiene compound to hydrolysis to form (2E,6Z)-2,6-nonadienal.

2. The process for preparing (2E,6Z)-2,6-nonadienal according to claim 1, wherein said hydrolysis is conducted in situ subsequently to the Wittig reaction.

3. The process for preparing (2E,6Z)-2,6-nonadienal according to claim 1, further comprising a step of preparing the (6,6-dialkoxy-4-hexenylidene)triarylphosphorane compound by deprotonation, in the presence of a base, of a 1,1-dialkoxy-2-hexenyltriarylphosphonium halide compound of the following general formula (3):

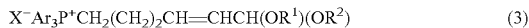

wherein Ar may be the same or different at each occurrence and is an aryl group, $R^1$ and $R^2$ are each independently a monovalent hydrocarbon group having 1 to 18 carbon atoms or together form a divalent hydrocarbon group, $R^1$-$R^2$, having 1 to 18 carbon atoms, and X is a halogen atom.

4. A process for preparing (2E)-cis-6,7-epoxy-2-nonenal of the following formula (8):

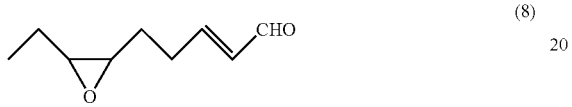

the process comprising at least
the process for preparing (2E,6Z)-2,6-nonadienal according to claim 1; and
a step of subjecting (2E,6Z)-2,6-nonadienal to epoxidation to form (2E)-cis-6,7-epoxy-2-nonenal.

5. A (6,6-dialkoxy-4-hexenylidene)triarylphosphorane compound of the following general formula (4):

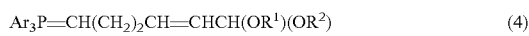

wherein Ar may be the same or different at each occurrence and is an aryl group, and $R^1$ and $R^2$ are each independently a monovalent hydrocarbon group having 1 to 18 carbon atoms or together form a divalent hydrocarbon group, $R^1$-$R^2$, having 1 to 18 carbon atoms.

6. A 1,1-dialkoxy-2-hexenyltriarylphosphonium halide compound of the following general formula (3):

wherein Ar may be the same or different at each occurrence and is an aryl group, $R^1$ and $R^2$ are each independently a monovalent hydrocarbon group having 1 to 18 carbon atoms or together form a divalent hydrocarbon group, $R^1$-$R^2$, having 1 to 18 carbon atoms, and X is a halogen atom.

7. The process for preparing (2E,6Z)-2,6-nonadienal according to claim 2, further comprising a step of preparing the (6,6-dialkoxy-4-hexenylidene)triarylphosphorane compound by deprotonation, in the presence of a base, of a 1,1-dialkoxy-2-hexenyltriarylphosphonium halide compound of the following general formula (3):

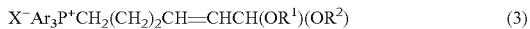

wherein Ar may be the same or different at each occurrence and is an aryl group, $R^1$ and $R^2$ are each independently a monovalent hydrocarbon group having 1 to 18 carbon atoms or together form a divalent hydrocarbon group, $R^1$-$R^2$, having 1 to 18 carbon atoms, and X is a halogen atom.

8. A process for preparing (2E)-cis-6,7-epoxy-2-nonenal of the following formula (8):

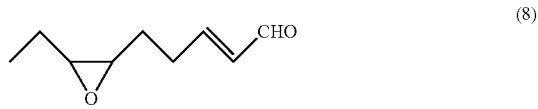

the process comprising at least
the process for preparing (2E,6Z)-2,6-nonadienal according to claim 2; and
a step of subjecting (2E,6Z)-2,6-nonadienal to epoxidation to form (2E)-cis-6,7-epoxy-2-nonenal.

9. A process for preparing (2E)-cis-6,7-epoxy-2-nonenal of the following formula (8):

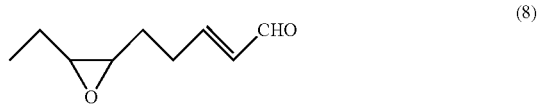

the process comprising at least
the process for preparing (2E,6Z)-2,6-nonadienal according to claim 3; and
a step of subjecting (2E,6Z)-2,6-nonadienal to epoxidation to form (2E)-cis-6,7-epoxy-2-nonenal.

10. A process for preparing (2E)-cis-6,7-epoxy-2-nonenal of the following formula (8):

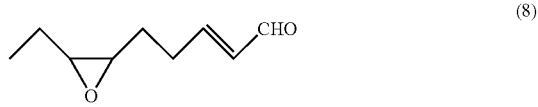

the process comprising at least
the process for preparing (2E,6Z)-2,6-nonadienal according to claim 7; and
a step of subjecting (2E,6Z)-2,6-nonadienal to epoxidation to form (2E)-cis-6,7-epoxy-2-nonenal.

* * * * *